United States Patent [19]

Levitt et al.

[11] 4,379,717
[45] Apr. 12, 1983

[54] METHOD OF CONTROLLING WEEDS IN CONIFERS

[75] Inventors: George Levitt; Russell C. Weigel, Jr., both of Wilmington, Del.

[73] Assignee: E. I. Du Pont de Nemours and Company, Wilmington, Del.

[21] Appl. No.: 234,236

[22] Filed: Feb. 13, 1981

[51] Int. Cl.³ .............................................. A01N 43/54
[52] U.S. Cl. .......................................... 71/92; 71/93; 71/86; 71/120
[58] Field of Search ............................................. 71/92

[56] References Cited

U.S. PATENT DOCUMENTS 4,169,719 10/1979 Levitt ...................................... 71/92

FOREIGN PATENT DOCUMENTS 7687 2/1980 European Pat. Off. .

OTHER PUBLICATIONS

Hinton et al., "Site Preparation and Regeneration, etc.;" (1972) CA 77, No. 110452w, (1972).
Fitzgerald et al., "Herbaceons Weed Control, etc.;" (1979) CA 92, No. 123272x, (1980).
Ahrens, "Chemical Control of Crabgrass, etc.;" (1971), CA 74, No. 123,931q, (1971).

Van Dorsser, "Current Research into Weed, etc.;" (1971), CA 76, No. 95658b, (1972).

*Primary Examiner*—Glennon H. Hollrah

[57] ABSTRACT

The application of certain sulfonylurea compounds to stands of conifer plants such as loblolly pine controls undesired vegetation without adverse effects on the conifers. These compounds have the formula:

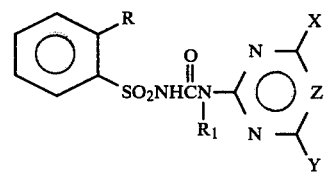

wherein
R is Cl or $CO_2R_2$ where $R_2$ is $C_1$-$C_4$ alkyl, $C_3$-$C_4$ alkenyl, $CH_2CH_2OCH_3$ or $CH_2CH_2Cl$;
$R_1$ is H or $CH_3$;
X is $CH_3$, $OCH_3$, $OC_2H_5$ or $CH_2OCH_3$;
Y is $CH_3$ or $OCH_3$; and
Z is CH or N; or
an agriculturally acceptable salt thereof.

6 Claims, No Drawings

METHOD OF CONTROLLING WEEDS IN CONIFERS

BACKGROUND OF THE INVENTION

1. Field of the Invention

This invention relates to methods of controlling undesired vegetation in conifers.

2. Prior Art

Conifer plants in cultivation generally must compete with other plants (weeds) for available light, moisture, and nutrients. Because of the competition for scarce resources, the conifers do not grow as quickly as they could without the competition. Indeed it is known that the number of years needed to develop a conifer crop can be reduced if good weed control practices are employed.

Hexazinone is used commercially for weed control in stands of various conifers. However, the need exists for additional products with high activity and possibly a different spectrum of weed control.

A wide variety of sulfonylurea compounds are known as broad spectrum herbicides and plant growth regulants. For example, U.S. Pat. No. 4,127,405, issued Nov. 28, 1978 and U.S. Pat. No. 4,169,719, issued Oct. 2, 1979, describe a number of triazine and pyrimidine compounds respectively for the above uses. Compounds useful in the present invention are described in published European Pat. No. 7687, published on Feb. 6, 1980.

SUMMARY OF THE INVENTION

According to the present invention there is provided a method for controlling undesired vegetation in conifers comprising: applying to the locus of said conifers an effective amount of a compound of the formula:

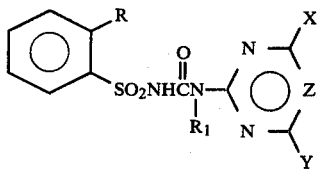

wherein

R is Cl or $CO_2R_2$ where $R_2$ is $C_1$–$C_4$ alkyl, $C_3$–$C_4$ alkenyl, $CH_2CH_2OCH_3$ or $CH_2CH_2Cl$;

$R_1$ is H or $CH_3$;

X is $CH_3$, $OCH_3$, $OC_2H_5$ or $CH_2OCH_3$;

Y is $CH_3$ or $OCH_3$; and

Z is CH or N; or an agriculturally acceptable salt thereof.

DETAILED DESCRIPTION OF THE INVENTION

It has been discovered that the compounds of Formula I above when applied at an effective amount to the locus of conifers result in the control of undesired vegetation such as weeds without adverse effects on the conifers. Preferred compounds in increasing order for their higher activity are those compounds of Formula I where:

(a) $R_1$ is H;

(b) X is $CH_3$ or $OCH_3$; and (c) R is Cl or $CO_2R_2$, where $R_2$ is $CH_3$ or $CH_2CH=CH_2$.

Specifically preferred compounds are:

(a) Methyl 2-[[(4,6-dimethylpyrimidin-2-yl)aminocarbonyl]aminosulfonyl]benzoate;

(b) Methyl 2-[[(4-methoxy-6-methyl-1,3,5-triazin-2-yl)aminocarbonyl]aminosulfonyl]benzoate;

(c) (1-propenyl) 2-[[(4,6-dimethoxypyrimidin-2-yl)aminocarbonyl]aminosulfonyl]benzoate; and (d) 2-chloro-N-[(4-methoxy-6-methyl-1,3,5-triazin-2-yl)aminocarbonyl]benzenesulfonamide.

The preparation of compounds where R is Cl and their formulation are described in the aforesaid U.S. Pat. No. 4,127,405; and the preparation of compounds where R is $CO_2R_2$ and their formulation are described in the aforesaid published European Patent No. 7687. The disclosures in these patents on preparation and formulation are hereby incorporated by reference.

Compounds of Formula I are useful in the present invention for the control of undesired vegetation in conifer establishments (Pinus spp., etc.) such as tree nurseries, forests, reforestation areas, etc. In particular, the compounds useful in the present invention are tolerant to loblolly pine (*Pinus taeda*). The conifers may be seedling plants or more mature plants including established trees. Some of these compounds are more suited for the control of grassy weeds, and others are more suited for the control of broadleaf weeds (both herbaceous and woody, including undesired trees). The compounds provide control of undesired vegetation whether applied pre-emergence or post-emergence to it. Herbicidal activity is maximized if the compounds are applied just prior to emergence in pre-emergence applications or when the weeds are actively growing in post-emergence applications. Combinations of two or more of the compounds of the present invention may be applied, with broader-spectrum control of undesired vegetation the result of said combinations. These compounds may also be combined with other herbicidal products such as hexazinone\*, ammonium salt of fosamine\*\*, diuron\*\*\*, certain substituted triazines, and others where reference to the known properties of the compounds indicates the desirability of such combinations. The combinations may provide broader-spectrum weed control and may extend the duration of weed control in reference to the weed control that is provided by the application of a single compound.

\*Hexazinone: 3-cyclohexyl-6-(dimethylamino)-1-methyl-1,3,5-triazine-2,4(1H,3H)-dione
\*\* Fosamine: ethyl hydrogen(aminocarbonyl)phosphonate
\*\*\*Diuron: 3-(3,4-dichlorophenyl)-1,1-dimethylurea In order to obtain control of undesired vegetation in conifer establishments, the compounds of the present invention are applied to the locus of the conifer trees at an application rate of from about 0.01–4 kilograms/hectare (preferably about 0.05 to 2 kg/ha), depending on the particular compound chosen, the weed population, conifer species, soil type, etc. Normally the compounds are formulated to maximize their performance in the field. The compounds may be applied as overall sprays, directed sprays, soil treatments, granules, pellets, etc.

Alternatively, the compounds may be applied to an area prior to the planting of conifers in the area.

The utility of the compounds of Formula I was discovered in greenhouse tests which are presented as Examples 1, 2 and 3. The data in Examples 1, 2 and 3 are presented in the form of plant response ratings, which consist of a number and a letter. The number represents the extent of the response and ranges from zero to ten with zero indicating no response and ten indicating 100% response. The letter describes the type of response, with "B" indicating burn (acute response), "C" indicating chlorosis-necrosis (chronic response), "G" indicating growth retarded, "H" indicating formative effect (malformation or hormone type), "P" indicating terminal bud injury, "W" indicating wilt, and "X" indicating axillary stimulation. In order to arrive at the plant response ratings, reference is made first to a control, which is considered to have zero response.

In the examples, parts and percentages are by weight and the compounds used have the following formulas:

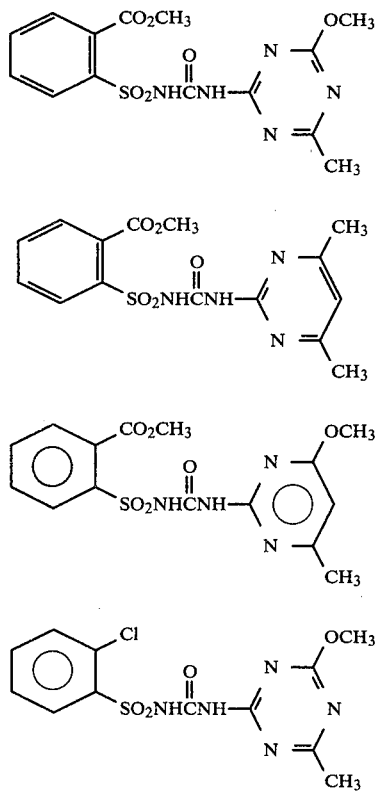

Compound 1

Compound 2

Compound 3

Compound 4

EXAMPLE 1

The test samples were dissolved in a solvent containing mostly (over 90%) acetone plus a little water, glycerin, and 0.21% polyoxyethylene (20) sorbitan monolaurate and applied as overall sprays on several woody plants, each situated in plastic pots containing soil. The plants were maintained in a greenhouse, and plant response ratings were taken at approximately one week and nine weeks after application and are presented in Table I.

TABLE I

| | Compound 4 | | | |
|---|---|---|---|---|
| | Treatment Rate kg ai/ha | | | |
| | 0.125 | | 0.5 | |
| | 1 wk. | 9 wks. | 1 wk. | 9 wks. |
| Willow* | 9B | 10B | 9B | 10B |
| Forsythia* | 1C | 10C | 3C | 10C |
| Loblolly Pine* | 0 | 0 | 0 | 5H |
| Apple* | 9C | 10C | 9C | 10C |

*Salix sp., Forsythia sp., *Pinus taeda*, and Malus sp., respectively.

EXAMPLE 2

The test compounds were dissolved in the same solvent described in Example 1 and applied as overall sprays on several woody plants, each situated in plastic pots containing soil. The plants were maintained in a greenhouse, and plant response ratings were taken at approximately one week and nine weeks after application, and are presented in Table II.

TABLE II

| | Compound 1 | | | | | |
|---|---|---|---|---|---|---|
| | Treatment Rate kg ai/ha (a.i. = active ingredient) | | | | | |
| | 0.016 | | 0.031 | | 0.125 | |
| | 1 wk. | 9 wks. | 1 wk. | 9 wks. | 1 wk. | 9 wks. |
| Privet* | 3C | 10C | 3C | 10C | 3C | 10C |
| Willow* | 3B | 9B | 3B | 9B | 3B | 10B |
| Forsythia* | 1C | 10C | 1C | 10C | 1C | 10C |
| Loblolly Pine* | 0 | —** | 0 | —** | 1C | —** |
| Apple* | 6B | 10B | 9B | 10B | 5B | 10B |

| | Compound 2 | | | | | |
|---|---|---|---|---|---|---|
| | Treatment Rate kg ai/ha | | | | | |
| | 0.016 | | 0.031 | | 0.125 | |
| | 1 wk. | 9 wks. | 1 wk. | 9 wks. | 1 wk. | 9 wks. |
| Privet* | 3C | 10C | 3C | 7C | 4C | 10C |
| Willow* | 9B | 10B | 5B | 9B | 8B | 10B |
| Forsythia* | 2C | 8G | 2C | 5G | 6C | 10C |
| Loblolly Pine* | 0 | —** | 0 | —** | 0 | —** |
| Apple* | 4B | 9G,3B | 3B | 9G,5B | 3B | 9B |

| | Compound 4 | | | | | | | |
|---|---|---|---|---|---|---|---|---|
| | Treatment Rate kg ai/ha | | | | | | | |
| | 0.016 | | 0.031 | | 0.062 | | 0.125 | |
| | 1 wk. | 9 wks. | 1 wk. | 9 wks. | 1 wk. | 9 wks. | 1 wk. | 9 wks. |
| Privet* | 3C | 10C | 3C | 10C | 3C | 10C | 2C | 10C |
| Willow* | 5B | 9G,5B | 5B | 9B | 9B | 9B | 4B | 9B |
| Forsythia* | 3C | 7C | 3C | 10C | 4C | 10C | 4C | 10C |
| Loblolly Pine* | 0 | —** | 0 | —** | 0 | —** | 0 | —** |
| Apple* | 3B | 10B | 6B | 10B | 5B | 10B | 9B | 10B |

*Ligustrum sp., Salix sp., Forsythia sp., *Pinus taeda*, and Malus sp., respectively.
**indicates that no rating was made (because of variability).

EXAMPLE 3

The test compounds were dissolved in the same solvent described in Example 1 and applied as an overall spray on several woody plants, each situated in plastic pots containing soil. The plants were maintained in a greenhouse, and plant response ratings were taken at approximately one week and eight weeks after application, and are presented in Table III.

TABLE III

| | Compound 3 | | | | | |
|---|---|---|---|---|---|---|
| | Treatment Rate kg ai/ha | | | | | |
| | 0.016 | | 0.031 | | 0.125 | |
| | 1 wk. | 8 wks. | 1 wk. | 8 wks. | 1 wk. | 8 wks. |
| Privet* | 0 | 10C | 1C | 10C | 0 | 10C |
| Willow* | 2B | 10G | 5U,1B | 9C | 6B | 9C |
| Forsythia* | 0 | 10C | 1C | 10G,3C | 1C | 10G, 4C |
| Loblolly Pine* | 0 | 0 | 0 | 0 | 0 | 3H |
| Apple* | 2W | 9G,2X, 1C | 4W | 9G,3C | 4W,4B | 10B |

| | Compound 1 | |
|---|---|---|
| | Treatment Rate kg ai/ha | |
| | 0.016 | 0.031 |

TABLE III-continued

|  | 1 wk. | 8 wks. | 1 wk. | 8 wks. |
|---|---|---|---|---|
| Privet* | 0 | 10C | 0 | 10C |
| Willow* | 4B,5U | 10C | 7U,2B | 9C |
| Forsythia* | 1C | 9G | 1C | 10C |
| Loblolly Pine* | 0 | 0 | 0 | 5G |
| Apple* | 2W,2B | 10B | 3W,3B | 10B |

| | Compound 4 Treatment Rate kg ai/ha | | | | | | | |
|---|---|---|---|---|---|---|---|---|
| | 0.016 | | 0.031 | | 0.062 | | 0.125 | |
| | 1 wk. | 8 wks. | 1 wk. | 8 wks. | 1 wk. | 8 wks. | 1 wk. | 8 wks. |
| Privet* | 1C | 10C | 1C | 10C | 1C | 10C | 1C | 10C |
| Willow* | 3U, 1B | 9G, 5X | 2U, 2B | 9G, 5X | 7B | 9C | 7U, 2B | 9C |
| Forsythia* | 0 | 5G | 0 | 9C | 1C | 10C | 1C | 10C |
| Loblolly Pine* | 0 | 0 | 0 | 0 | 0 | 3C | 0 | 9G,2P, 2X |
| Apple* | 2W | 10C | 2W | 10C | 3W | 10C | 4W, 3B | 10B |

*Scientific names appear in Table II.

Examples 1, 2 and 3 demonstrate control of woody vegetation (shrubs and trees) and tolerance to loblolly pine. The following examples (Examples 4, 5, 6 and 7) are field tests and further demonstrate the utility of the compounds of the present invention.

EXAMPLE 4

A series of tests were initiated in North Carolina, Apr. 8, 1980, using single row plots 1.52×9.14 meters in size. Wettable powder formulations of the compounds were applied in water as overall sprays on dormant second year loblolly pine trees. The compounds were applied pre-emergence to weeds (primarily a Panicum sp. infestation). Each treatment was replicated three times; the following table, Table IV, summarizes the data from the test. In Table IV, the response of loblolly pine is presented as "tree growth" with zero including no growth and ten indicating maximum growth. Percent weed control and tree growth measurements were taken on Aug. 7 and also Sept. 15, 1980.

TABLE IV

| Compound | Treatment Rate, kg ai/ha | Percent Weed Control | | Tree Growth | |
|---|---|---|---|---|---|
| | | 8/7/80 | 9/15/80 | 8/7/80 | 9/15/80 |
| 2 | 0.56 | 91.0 | 81.7 | 10.0 | 10.0 |
| | 1.12 | 81.0 | 80.0 | 9.0 | 9.3 |
| | 2.24 | 92.7 | 90.0 | 10.0 | 10.0 |
| 1 | 0.56 | 87.7 | 68.3 | 9.3 | 9.3 |
| | 1.12 | 88.3 | 66.7 | 8.0 | 8.7 |
| | 2.24 | 96.0 | 85.0 | 9.0 | 8.0 |
| 4 | 0.56 | 46.7 | 38.3 | 9.3 | 8.7 |
| | 1.12 | 75.0 | 53.3 | 10.0 | 8.7 |
| | 2.24 | 93.3 | 76.7 | 9.3 | 8.3 |
| Cpd. 2 Plus Hexazinone | 0.56 to 0.56 | 95.0 | 85.0 | 10.0 | 9.3 |
| Cpd. 1 Plus Hexazinone | 0.56 to 0.56 | 94.0 | 82.7 | 8.0 | 8.3 |
| Cpd. 4 Plus Hexazinone | 0.56 to 0.56 | 67.7 | 73.3 | 8.0 | 8.3 |
| Control (Non-Treated) | — | 0.0 | 0.0 | 9.0 | 8.7 |

EXAMPLE 5

Another series of tests was initiated in North Carolina in 1980. One series was conducted on Apr. 8, 1980 on dormant first year loblolly pine trees (pre-emergence to weeds); another series was conducted on June 17, 1980 on first year trees (post-emergence to weeds). Again, the weed population was primarily Panicum sp. The test was conducted in a similar fashion to Example 4 except as otherwise indicated above. Table V presents a summary of the data from this test.

TABLE V

| PRE-TREATMENT (APPLIED 4/8/80) | | | | | |
|---|---|---|---|---|---|
| Compound | Treatment Rate, kg ai/ha | Percent Weed Control | | Tree Growth | |
| | | 8/7/80 | 9/15/80 | 8/7/80 | 9/15/80 |
| 2 | 0.56 | 88.3 | 83.3 | 8.3 | 8.0 |
| | 1.12 | 95.7 | 93.0 | 9.0 | 8.0 |
| | 2.24 | 98.3 | 96.0 | 7.3 | 7.0 |
| 1 | 0.56 | 84.3 | 80.0 | 9.0 | 8.7 |
| | 1.12 | 78.3 | 60.0 | 6.3 | 6.7 |
| | 2.24 | 98.3 | 88.7 | 7.0 | 6.7 |
| 4 | 0.56 | 86.0 | 75.0 | 7.3 | 7.0 |
| | 1.12 | 79.7 | 56.7 | 6.0 | 6.0 |
| | 2.24 | 88.3 | 80.0 | 8.3 | 7.3 |
| Cpd. 2 Plus Hexazinone | 0.56 to 0.56 | 96.0 | 92.7 | 7.7 | 8.3 |
| Cpd. 1 Plus Hexazinone | 0.56 to 0.56 | 86.3 | 78.0 | 9.0 | 6.3 |
| Cpd. 4 Plus Hexazinone | 0.56 to 0.56 | 98.7 | 96.3 | 9.3 | 8.7 |
| Control (Non-Treated) | — | 76.0 | 54.3 | 9.7 | 8.7 |

| POST-TREATMENTS (APPLIED 6/17/80) | | | | | | |
|---|---|---|---|---|---|---|
| Compound | Treatment Rate, kg ai/ha | Number of trees[1] 6/17/80 | Weed Control | | Tree Growth | |
| | | | 8/7/80 | 9/15/80 | 8/7/80 | 9/15/80 |
| 2 | 0.56 | 4.3 | 96.3 | 97.0 | 9.7 | 9.7 |
| | 1.12 | 4.3 | 98.3 | 95.7 | 9.7 | 8.7 |
| | 2.24 | 4.3 | 99.0 | 98.7 | 8.3 | 7.0 |
| 1 | 0.56 | 5.0 | 97.7 | 95.3 | 8.7 | 7.3 |
| | 1.12 | 3.0 | 94.7 | 91.3 | 4.7 | 5.3 |
| | 2.24 | 4.0 | 99.0 | 98.3 | 6.3 | 5.7 |
| 4 | 0.56 | 5.0 | 99.0 | 98.7 | 8.7 | 7.7 |
| | 1.12 | 4.0 | 97.3 | 91.3 | 5.7 | 6.0 |
| | 2.24 | 3.7 | 98.7 | 96.0 | 7.7 | 7.0 |
| Cpd. 2 Plus Hexazinone | 0.56 to 0.56 | 4.0 | 97.7 | 96.3 | 8.3 | 7.3 |
| Cpd. 1 Plus Hexazinone | 0.56 to 0.56 | 3.3 | 96.0 | 85.0 | 5.7 | 6.7 |
| Cpd. 4 Plus Hexazinone | 0.56 to 0.56 | 2.7 | 91.7 | 88.3 | 6.0 | 4.3 |
| Control (Non-treated) | — | 4.0 | 50.0 | 57.7 | 9.0 | 7.7 |

[1] The mean number of trees present in the three replicates. Living trees weren't counted on 4/8/80 because it was too early to determine survival from the preceeding winter.

EXAMPLE 6

On Aug. 5, 1980, a wettable powder formulation of test compound 1 was applied in water to a plot 15.24×6.096 meters in size, located near Houstonville, Ky. Observations on the extent of resulting defoliation were taken on Sept. 9, 1980 and appear in Table VI.

TABLE VI

|  | Percent Defoliation | |
| --- | --- | --- |
|  | Compound 1 | Control (Not Treated) |
| Treatment Rate, kg ai/ha | 1.96 | — |
| Sassafras* | 0 | 0 |
| Ash | 100 | 0 |
| American Elm | 100 | 0 |
| Redbud | 100 | 0 |
| Sugar Maple | 100 | 0 |
| Blackberry | 100 | 0 |
| White Oak | 60 | 0 |
| Sumac | 5 | 0 |

*Sassafras sp., Fraxinus sp., *Ulmus americana,* Cercis sp., Acer sp., Rubus sp., Quercus sp., and Rhus sp., respectively.

Table VI demonstrates high activity against a number of deciduous trees.

EXAMPLE 7

In another test, compound 2* was applied in Oregon on Apr. 25, 1980 as a broadcast spray over-the-top of nursery beds while the conifers present were still dormant. The conifers in the test were Douglas fir (*Pseudotsuga taxifolia*), Noble fir (*Abies procera*) and ponderosa pine (*Pinus ponderosa*) which were grown from seed and transplanted (bare root) into the test area (machine transplant) on Apr. 15, 1980 when they were two years old. The soil in the test area is a silt loam type with 5% organic matter. One inch of sprinkler irrigation was applied to the test area every six days. It was observed that the trees in the test were somewhat smaller than normal two year old transplants. Observations were made 83 days after treatment and are shown in Table VII.

*Compound 4 was also applied in the present test. Exact data are not available at the present time; however, the conifers were injured at the lowest application rate, 0.035 kg ai/ha.

TABLE VII

| Treatment Rate kg ai/ha | 0.035 | 0.07 | 0.14 | 0.28 |
| --- | --- | --- | --- | --- |
| PERCENT GROWTH REDUCTION | | | | |
| Douglas Fir | 30 | 40 | 50 | ~60 |
| Noble Fir | 10 | 25 | ~48 | ~68 |
| Ponderosa Pine | 15 | 25 | ~35 | ~33 |
| PERCENT WEED CONTROL | | | | |
| Groundsel* | ~98 | ~98 | ~98 | ~98 |
| Chickweed | ~98 | ~98 | ~98 | ~98 |
| Shepherd's Purse | ~98 | ~98 | ~98 | ~98 |

*Senecio sp., (probably Stellaria sp.), *Capsella bursa-pastoris.*

In reviewing the results of Example 7, it seems likely that lower application rates may have provided satisfactory weed control while reducing conifer injury to even lower levels than those that were reported. Other factors that may have reduced the conifer tolerance in the example include the irrigation schedule, soil type and the fact that applications were made soon after transplanting of the bare-rooted plants. Nevertheless, it is apparent that the conifers are much more tolerant to the compound that was applied than are the weed species.

What is claimed is:

1. A method for controlling undesired vegetation in conifers comprising: applying to the locus of said conifers an effective amount of a compund of the formula:

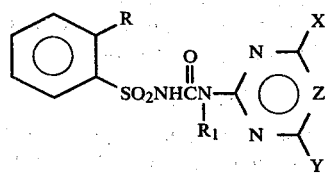

wherein
R is $CO_2R_2$ where $R_2$ is $C_1$–$C_4$ alkyl;
$R_1$ is H or $CH_3$;
X is $CH_3$, or $OCH_3$;
Y is $CH_3$ or $OCH_3$; and
Z is CH; or
an agriculturally acceptable salt thereof.

2. The method of claim 1 wherein $R_1$ is H.
3. The method of claim 2 wherein R is $CO_2R_2$, where $R_2$ is $CH_3$.
4. The method of claim 1 wherein the compound is Methyl 2-[[(4,6-dimethylpyrimidin-2-yl)aminocarbonyl]aminosulfonyl]benzoate.
5. The method of claims 1, 2, 3 or 4 wherein the conifer is loblolly pine.
6. The method of claim 5 wherein the compound is applied at a rate of about 0.01–4 kg/ha.

* * * * *